Figure 1:
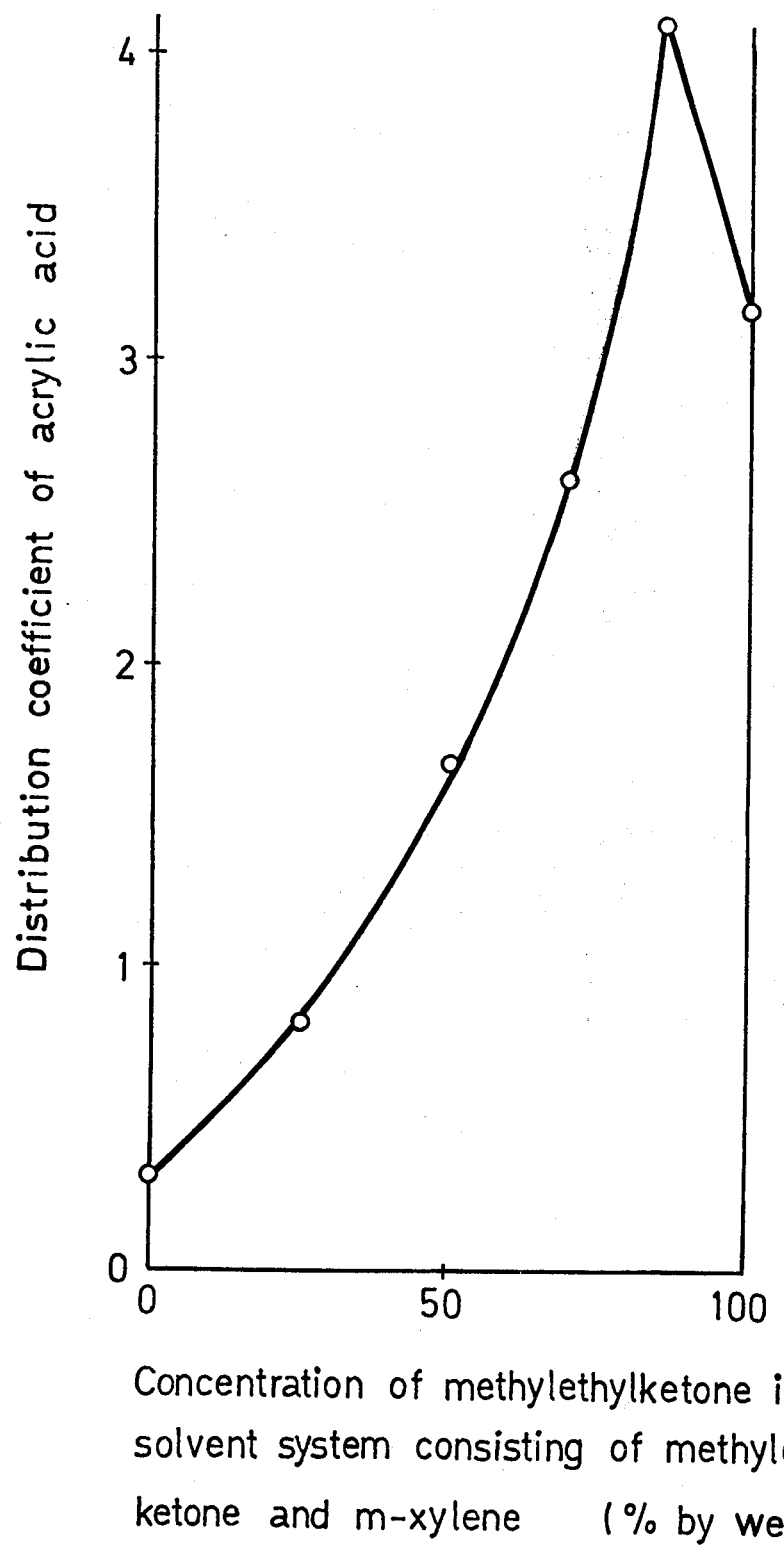

United States Patent [19]
Ohrui et al.

[11] 3,968,153
[45] July 6, 1976

[54] EXTRACTION OF ACRYLIC ACID AND/OR METHACRYLIC ACID WITH A SOLVENT MIXTURE OF METHYLETHYLKETONE AND XYLENE OR ETHYLBENZENE

[75] Inventors: Tetsuya Ohrui, Niihama; Yasuhito Sakakibara, Saijo; Yukinaga Aono, Niihama; Michio Kato, Niihama; Hiroshi Takao, Niihama; Masami Ayano, Niihama, all of Japan

[73] Assignee: Sumitomo Chemical Company, Limited, Japan

[22] Filed: May 10, 1973

[21] Appl. No.: 358,997

[30] Foreign Application Priority Data
May 23, 1972 Japan.................................. 47-51396

[52] U.S. Cl................................ 260/526 N; 203/15; 203/51; 203/62; 203/69
[51] Int. Cl.²................................ C07C 57/00
[58] Field of Search.................... 203/15, 43–46, 203/51, 63, 70, DIG. 21, 62, 69; 260/526 N

[56] References Cited
UNITED STATES PATENTS

| | | | |
|---|---|---|---|
| 2,386,365 | 10/1945 | Staudinger et al. | 203/58 |
| 2,922,815 | 1/1960 | Faerber | 260/526 N |
| 3,337,740 | 8/1967 | Gray et al. | 260/526 N |
| 3,414,485 | 12/1968 | Speed | 203;260/15;526 N |
| 3,433,831 | 3/1969 | Yomiyama et al. | 260/526 N |
| 3,478,093 | 11/1969 | Nonnenmacher et al. | 260/526 N |
| 3,657,332 | 4/1972 | Sennewald et al. | 260/526 N |
| 3,692,829 | 9/1972 | Sennewald et al. | 260/526 N |
| 3,781,332 | 12/1973 | Sato et al. | 260/526 N |
| 3,798,264 | 4/1974 | Kubota et al. | 203/15 |

*Primary Examiner*—Wilbur L. Bascomb, Jr.
*Attorney, Agent, or Firm*—Steward and Kolasch, Ltd.

[57] ABSTRACT

A method for extraction of acrylic acid and/or methacrylic acid from a solution containing the same by treating the said solution with an organic solvent, which is characterized by using a mixture of methylethylketone and a xylene as the organic solvent. By such method, the extraction of acrylic acid and/or methacrylic acid is accomplished efficiently and economically.

9 Claims, 2 Drawing Figures

Concentration of methylethylketone in the solvent system consisting of methylethylketone and m-xylene (% by weight)

Concentration of methylethylketone in the solvent system consisting of methylethylketone and m-xylene   (% by weight)

EXTRACTION OF ACRYLIC ACID AND/OR METHACRYLIC ACID WITH A SOLVENT MIXTURE OF METHYLETHYLKETONE AND XYLENE OR ETHYLBENZENE

The present invention relates to a method for extraction of acrylic acid and/or methacrylic acid from a solution containing at least one of them.

The separation of acrylic acid and/or methacrylic acid (hereinafter referred to as "(meth)acrylic acid") from an aqueous solution containing at least one of them can be accomplished by distilling out water from the aqueous solution and recovering (meth)acrylic acid as the bottom residue. The industrial application of this procedure is, however, not economical, because the concentration of (meth)acrylic acid is usually quite low and it is necessary to draw off a large amount of water by the distillation. Thus, the separation of (meth)acrylic acid from an aqueous solution containing the same is ordinarily effected in industry by extraction using any appropriate solvent.

For the extraction of (meth)acrylic acid, there are known various solvents. However, none of the known solvents is satisfactory. For instance, hydrocarbons (e.g. petroleum ether, benzene, toluene), halogenated hydrocarbons (e.g. chloroform, carbon tetrachloride, dichloroethane, trichloroethylene, tetrachloroethylene) and ethers (e.g. diethyl ether, diisopropyl ether) are those to which (meth)acrylic acid gives lower values in the distribution coefficient (K) as determined according to the following equation:

$$K = \frac{\text{Concentration (\% by weight) of (meth)acrylic acid in the solvent layer}}{\text{Concentration (\% by weight) of (meth)acrylic acid in the water layer}}$$

and therefore it is necessary to use such solvents in relatively large amounts so that the apparatuses for extraction and recovery are made large. Further, for instance, some ketones (e.g. methylethylketone) are excellent in the distribution coefficient but dissolve well in water so that the loss thereof is large.

As the result of the study seeking a more favorable solvent for industrial extraction of (meth)acrylic acid, it has been found that a mixture of methylethylketone and a xylene in a certain range of mixing ratio gives a higher distribution coefficient to (meth)acrylic acid than either methylethylketone or a xylene alone and is very suitable for the said use.

As to the combined use of some solvents for extraction of (meth)acrylic acid, there have been made some proposals. One of them is the use of a mixture of methyl acetate and a xylene [Japanese Patent Publication No. 1443/70]. The loss of methyl acetate into the water layer is, however, large and, when the concentration of the xylene in the solvent system is made higher to diminish such loss, the distribution coefficient of acrylic acid becomes lower and the extracting ability of the solvent system is decreased. Additionally, the use of methyl acetate may cause unfavorable chemical reactions such as esterification and ester exchange in the course of separation of acrylic acid from the extract by distillation to form methyl acrylate and acetic acid. The formation of acetic acid is substantially disadvantageous due to the difficulty in the separation of acetic acid from acrylic acid. Further, the by-production of methyl acrylate is the loss of acrylic acid.

Figure 2:
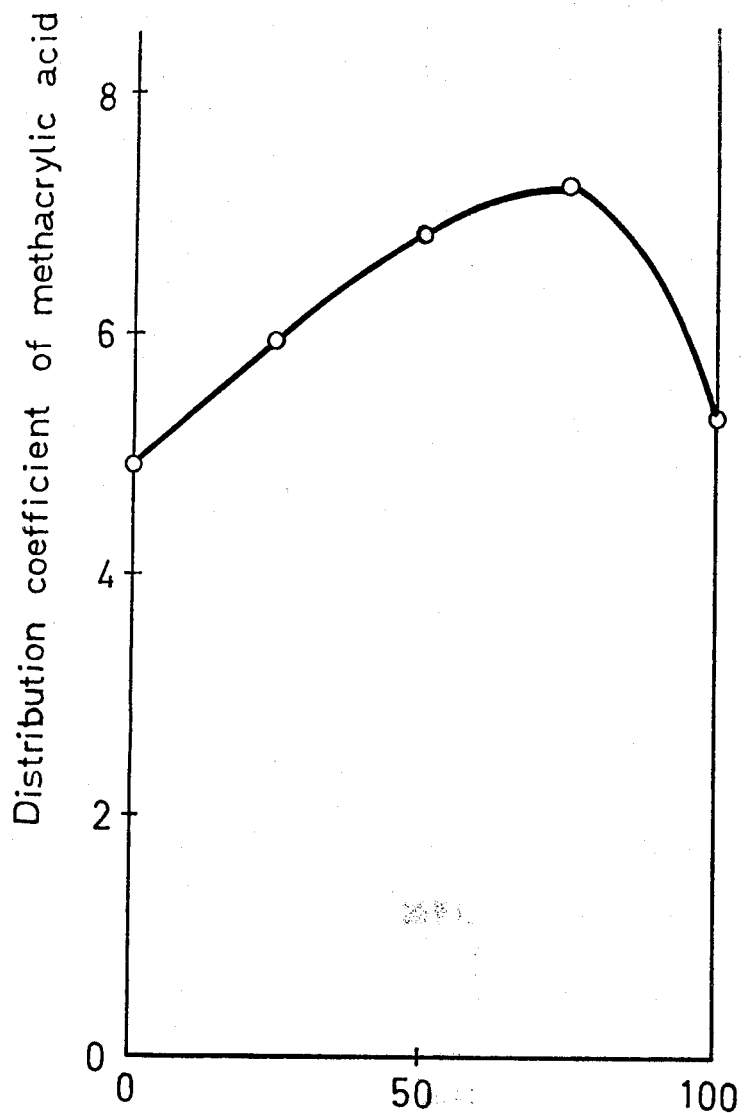

The solvent system consisting of methylethylketone and a to the present invention gives an excellent distribution coefficient to acrylic acid with a small loss into water. For instance, the relationship between the concentration (% by weight) of methylethylketone (on the axis of abscissa) in the solvent system consisting of methylethylketone and m-xylene and the distribution coefficient of acrylic acid (on the axis of ordinate) is as shown in FIG. 1 of the accompanying drawings. From this Figure, it is seen that the maximum distribution coefficient may be obtained using a mixture of methylethylketone and m-xylene in a weight ratio of about 4 : 1 to about 6 : 1. Further, the relationship between the concentration (% by weight) of methylethylketone (on the axis of abscissa) in the solvent system consisting of methylethyl ketone and m-xylene and the distribution coefficient of methacrylic acid (on the axis of ordinate) is as shown in FIG. 2 of the accompanying drawings. From this Figure, it is understood that the maximum distribution coefficient can be obtained in case of using a mixture of methylethylketone and m-xylene in a weight ratio of about 2.5 : 1 to about 3.5 : 1.

The loss of methylethylketone into the water layer is highly suppressed in the presence of the xylene, and the amount of methylethylketone lost into the aqueous solution is, for instance, less than 20 % by weight (on the basis of the amount of methylethylketone originally present in the solvent system), compared with that in case of using solely methylethylketone. Further, the xylene an form a azeotropic mixture of acetic acid. Thus, the elimination of the by-produced acetic acid from acrylic acid containing the same by distillation can be easily and favorably accomplished. Moreover, the xylene is an economically commercialized material, and the use of a solvent mixture containing the same is highly advantageous from the economical viewpoint.

According to the present invention, there is provided a method for extraction of (meth)acrylic acid from a solution containing at least one of them which comprises treating the said solution with a mixture of methylethylketone and a xylene to remove (meth)acrylic acid into the said mixture.

As the xylene, there may be used o-xylene, m-xylene, p-xylene, ethylbenzene or a mixture thereof.

For extraction of acrylic acid, it is preferred that the concentration of methylethylketone in the mixture be not less than about 75 percent, particularly from about 75 to about 95 % by weight. In order to extract methacrylic acid, it is desirable to use a mixture wherein the concentration of methylethylketone is not less than 15 percent, particularly from about 25 to about 95 % by weight. Thus, a mixture of methylethylketone and a xylene containing methylethylketone in a concentration from about 15 to about 95 % by weight may be usually employed.

The method of this invention is applicable to the extraction of (meth)acrylic acid not only from an aqueous solution containing the same but also from any other solution containing the same. Examples of the particularly preferred aqueous solution of (meth)acrylic acid to which the method of this invention is applied are those obtained by oxidation of propylene, isobutylene, acrolein and methacrolein, hydrolysis of acrylonitrile and the like. In such aqueous solution, there may be included some impurities (e.g. acrolein, acetic acid)

which do not cause any serious trouble in execution of the method of this invention.

The concentration of (meth)acrylic acid in the aqueous solution to be treated according to the present invention is not limitative and, when carried out industrially, is usually from about 1 to about 50 percent, particularly from about 10 to about 30 % by weight.

The extraction is carried out normally at a temperature from about 10° to about 70°C, preferably at a temperature between room temperature and 50°C. However, the execution at any temperature other than room temperature (around 20 to 30°C) does not produce any particular advantage. The extraction is usually performed under atmospheric pressure, although an elevated pressure (e.g. up to 5 atm.) may be adopted.

The extraction may be effected batchwise or continuously. The amount of the solvent system is usually from 0.1 to 10 times, preferably from 0.2 to 5 times, that of the aqueous solution depending on the initial and final concentrations of (meth)acrylic acid in the aqueous solution.

The recovery of acrylic acid and/or methacrylic acid from the extracting mixture can be carried out by any conventional technique known in the prior art, for example, by distillation.

Practical and presently preferred embodiments of the present invention are illustratively shown in the following Examples wherein % is by weight.

EXAMPLE 1

To 100 g of an aqueous solution of acrylic acid containing 10.0 % of acrylic acid, 60 g of a solvent mixture of methylethylketone and m-xylene are added. The resulting mixture is shaken well at 25°C under atmospheric pressure and allowed to stand. The organic solvent layer is separated from the water layer. Gas chromatographic analysis of the organic solvent layer gives the results as shown in FIG. 1 of the accompanying drawings, which indicates the relationship between the concentration of methylethylketone in the solvent system consisting of methylethylketone and m-xylene and the distribution coefficient of acrylic acid. From this Figure, it is seen that the distribution coefficient of acrylic acid abruptly increases with a higher concentration of methylethylketone in the solvent system consisting of methylethylketone and m-xylene and, when the concentration reaches to 80 %, becomes nearly equal to that in case of using solely methylethylketone. The maximum distribution coefficient is obtained when the concentration comes to around 85 %, and it is about 13 times and about 1.3 times that in case of using m-xylene solely and in case of using methylethylketone solely, respectively. Thus, it may be said that the most effective extraction of acrylic acid can be accomplished by the use of a mixture of methylethylketone and m-xylene wherein the concentration of methylethylketone is from 80 to 95 percent. Since the loss of methylethylketone into the water layer is highly suppressed in the presence of m-xylene, a lower concentration of methylethylketone in the solvent system is still operative from the industrial viewpoint.

By the use of a mixture of xylenes instead of m-xylene in the said solvent system, the similar results are obtained.

EXAMPLE 2

The operation is performed as in Example 1 but using 100 g of an aqueous solution of methacrylic acid containing 10.0 % of methacrylic acid. The results are shown in FIG. 2 of the accompanying drawings, which indicates the relationship between the concentration of methylethylketone in the solvent system consisting of methylethylketone and m-xylene and the distribution coefficient of methacrylic acid.

What is claimed is:

1. A method for the extraction of acrylic acid from a solution containing the same which comprises treating said solution with a solvent mixture of methylethylketone and at least one member selected from the group consisting of o-xylene, m-xylene, p-xylene and ethylbenzene wherein the concentration of the methylethylketone is from about 80 to 95% by weight at room temperature to transfer acrylic acid from said solution into the solvent mixture, the amount of the solvent mixture being 0.1 to 10 parts by weight to 1 part by weight of said solution.

2. The method according to claim 1, wherein the amount of the solvent mixture is 0.2 to 5 parts by weight per 1 part by weight of said solution.

3. The method according to claim 1, wherein the solution is an aqueous solution.

4. A method for the extraction of methacrylic acid from a solution containing the same which comprises treating said solution wth a solvent mixture of methylethylketone and at least one member selected from the group consisting of o-xylene, m-xylene, p-xylene and ethylbenzene wherein the concentration of the methylethylketone is from about 25 to 95% by weight at room temperature to transfer methacrylic acid into the solvent mixture, the amount of the solvent mixture being 0.1 to 10 parts by weight to 1 part by weight of said solution.

5. The method according to claim 4, wherein the amount of the solvent mixture is 0.2 to 5 parts by weight per 1 part by weight of said solution.

6. The method according to claim 4, wherein said solution is an aqueous solution.

7. A method for the extraction of acrylic acid and/or methacrylic acid from a solution containing at least one of said materials which comprises treating said solution with a solvent mixture of methylethylketone and at least one member selected from the group consisting of o-xylene, m-xylene, p-xylene and ethylbenzene wherein the concentration of the methylethylketone is from about 80 to 95% by weight to transfer acrylic acid and/or methacrylic acid from said solution into the solvent mixture, the amount of the solvent mixture being 0.1 to 10 parts by weight to 1 part by weight of said solution.

8. The method according to claim 7, wherein the amount of said mixture is 0.2 to 5 parts by weight per 1 part by weight of said solution.

9. The method according to claim 7, wherein the solution is an aqueous solution.

* * * * *